United States Patent [19]

Bach, Jr. et al.

[11] Patent Number: 5,018,523
[45] Date of Patent: May 28, 1991

[54] APPARATUS FOR COMMON MODE STIMULATION WITH BIPOLAR SENSING

[75] Inventors: Stanley M. Bach, Jr., Shoreview; Douglas J. Lang, Arden Hills; David K. Swanson, Roseville; Roger W. Dahl, Andover, all of Minn.

[73] Assignee: Cardiac Pacemakers, Inc., St. Paul, Minn.

[21] Appl. No.: 512,363

[22] Filed: Apr. 23, 1990

[51] Int. Cl.⁵ .............................................. A61N 1/362
[52] U.S. Cl. .............................. 128/419 PG; 128/786; 128/902
[58] Field of Search ................. 128/419 PG, 696, 709, 128/786, 902

[56] References Cited

U.S. PATENT DOCUMENTS

| | | | |
|---|---|---|---|
| 3,614,954 | 10/1971 | Mirowski et al. | 128/419 D |
| 3,857,398 | 12/1974 | Rubin | 128/419 D |
| 4,549,548 | 10/1985 | Wittkampf et al. | 128/419 PG |
| 4,603,704 | 8/1986 | Mund et al. | 128/784 |
| 4,628,934 | 12/1986 | Pohndorf et al. | 128/419 PG |

Primary Examiner—William E. Kamm
Attorney, Agent, or Firm—Haugen and Nikolai

[57] ABSTRACT

An apparatus for stimulating and sensing evoked response to stimulus in the heart. First and second electrodes are in electrical contact with the heart, a third indifferent electrode is also in electrical contact with the heart. A pacemaker provides stimulus signals through the electrodes in the stimulating mode of operation. The first and second electrodes are switched through switching apparatus wherein in the first mode the first and second electrodes are maintained at equal electrical potentials, and in a second, sensing mode, the switch operates between the first and second electrodes so as to allow the first and second electrodes to act as bipolar sensing leads. Evoked response is sensed by a differential amplifier having a first differential input connected to the first electrode and a second differential input connected to the second electrode. The differential amplifier provides a differential signal which is proportional to the evoked cardiac response.

30 Claims, 3 Drawing Sheets

Fig.-3

APPARATUS FOR COMMON MODE STIMULATION WITH BIPOLAR SENSING

BACKGROUND OF THE INVENTION

This invention relates broadly to the art of implantable medical devices and, more particularly, to apparatus having first and second electrodes which deliver an electrical potential to body tissue in a common mode configuration and which operate as bipolar sensors when switched to a sensing mode. The invention is particularly useful for cardiac pacing systems, defibrillation apparatus, heart stroke volume rate adaptive pacemakers, cardioversion devices and the stimulation and measurement of other physiological events.

With respect to this invention's contribution to the art, it is helpful to first present some background on the state of the art. Present heart pacing systems pace and sense through the same electrodes, making it difficult to verify capture of cardiac tissue. The after-potentials following a pacing impulse are much greater than the evoked potentials of the myocardium so immediate detection of electrograms from the pacing electrode is very difficult, if not impossible, due to total swamping of the evoked response. Prior art systems have attempted to reduce the effects of such after-potentials by various methods.

For example, U.S. Pat. No. 4,343,312 to Cals, et al., discloses a physiological stimulating system, which in a pacemaker embodiment, delivers signals constituted of a series of alternating polarity pulses of respective time durations and signal levels in an attempt to minimize the resulting polarization at the point of delivery of such signals. Cals is trying to overcome the large after-potential signal at the electrode which occurs immediately after delivery of a negative-going stimulus pulse. Since it takes some time for this after-potential signal to dissipate, the signal has the effect of masking the evoked response which occurs shortly after application of the negative-going stimulus pulse employed by Cals.

Similarly, U.S. Pat. No. 3,924,641 to Weiss provides a biphasic current stimulation system in a attempt to avoid unfavorable interactions between electrodes and tissues caused by pulses of one polarity. A similar scheme is also taught by UK Patent Application GB 2,193,101A to Napholz entitled "Pacing Pulse Compensation". Napholz teaches a pacemaker which generates a triphasic stimulus wherein the first and third phases are positive pulses and the second is the negative stimulus. European patent application publication number 0308536 filed Sept. 24, 1987 entitled "Pacemaker Having Programmable Configuration" discloses a pacemaker having a programmable configuration including a plurality of solid state switches controlled by programmed data stored in memory. During the pacing mode of operation a first reference electrode is switchably connected to the most positive battery potential and during a sensing mode of operation, the first reference electrode is switchably connected to −0.5 volts. Such prior art techniques for eliminating after-potentials in a cardiac stimulation system are very complex. All of them require a significant delay before sensing of the evoked response can be accomplished in order to allow neutralization of the signal. If the delay is too long the evoked response may be lost entirely.

Other prior art techniques use similar electrode configurations and, instead of applying biphasic pulses, first apply a stimulation pulse and then tie the sensing electrodes together after the body tissue is stimulated. These schemes also require a significant delay to allow neutralization of the signal before sensing of the evoked response can be accomplished.

The present invention overcomes the perceived disadvantages of prior art devices in providing a system for a cardiac pacemaker including common mode stimulation apparatus with bipolar sensing apparatus so as to allow sensing of the evoked cardiac response almost immediately after application of the stimulation signal from a pacing device.

Figure 1:
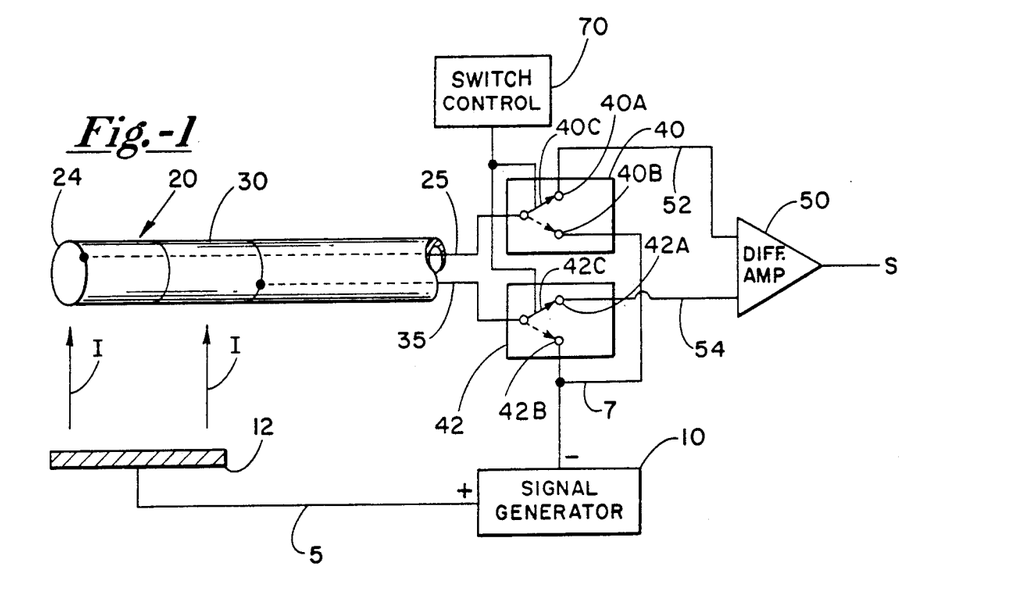
FIG. 1 is a schematic diagram of common mode stimulation apparatus with bipolar sensing employing the principles of this invention.
Figure 2:
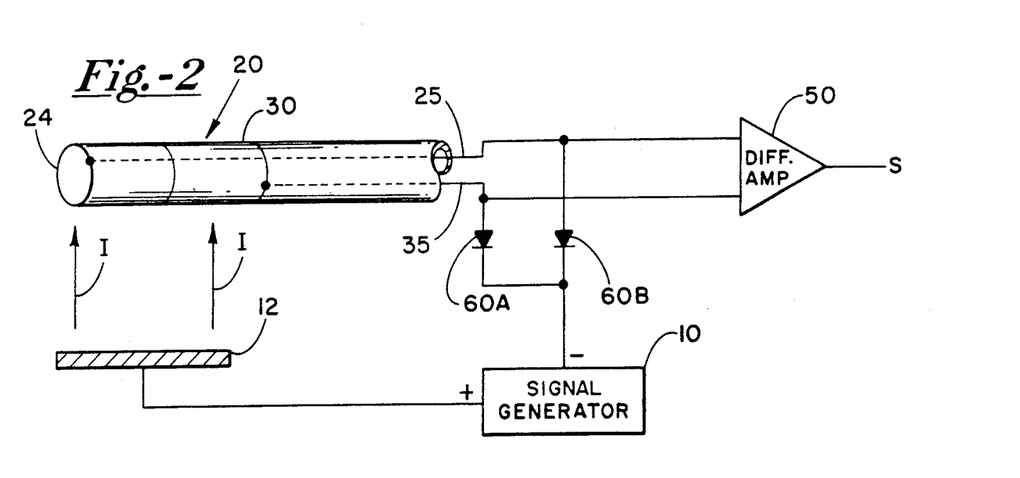
FIG. 2 is a schematic diagram of another aspect of the invention employing diode devices.

The pacing scheme provided by the present invention is a general method that permits capture verification through the use of bipolar sensing and pacing in parallel through both sensing electrodes to an indifferent electrode. The pacing and sensing method may be implemented using a switch or a pair of diodes as is shown in FIGS. 1 and 2. The electrode configuration for this pacing method may vary, ranging from a bipole located on a catheter to an epicardial bipole electrode or electrode pair. As described above, the success of this pacing method requires that the two bipolar electrodes be designed to have similar pacing after-potentials so that the common pacing signal can be rejected by the bipolar sensing amplifier. This apparatus is improved further by electrode design techniques which reduce electrode after-potentials such as is discussed in the assignee's application for a "Porous Electrode With Enhanced Reactive Surface", filed Mar. 20, 1989, Ser. No. 07/325/764 which is incorporated herein by reference.

As will be appreciated by those skilled in the art, the scope of the invention extends beyond the field of pacemakers. For example, the teachings of the invention are also applicable to defibrillation apparatus, heart stroke volume sensing apparatus, cardioversion devices and measurement and stimulation of other physiological events. Generally, the invention can be employed in virtually any situation wherein a pulsed electrical potential is applied to a human body and one desires to measure the body's response to the application of the pulsed electrical potential.

SUMMARY OF THE INVENTION

It is an object of this invention to provide a pacing system for delivering stimulus signals to a patient's heart, wherein the sensed polarization immediately following delivery of a stimulus signal is minimized so as to allow more immediate signal detection of the evoked cardiac depolarization or repolarization signals which are present in the evoked cardiac response.

It is yet another object of this invention to provide almost immediate sensing of evoked responses to pacing, cardioversion, anti-tachycardia stimulation signals and any other type of electrical potential applied to the body tissue for the purpose of influencing body function.

It is yet another object of this invention to provide an improved pacing system and method for threshold tracking.

It is yet another object of this invention to provide apparatus for sensing a response in body tissue wherein the response results from an electrical potential applied to the body tissue for a limited duration by electrical contacts other than the sensing contacts.

It is yet another object of the invention to provide an improved apparatus for applying an electrical potential to body tissue and sensing the response to the applied electrical potential wherein the same electrodes are used to apply the electrical potential and measure the response while minimizing the effects of artifacts caused by after-potentials on the electrodes.

In accordance with the above, in one aspect of the invention there is provided apparatus for stimulating and sensing evoked cardiac response to a stimulus signal in the heart. The apparatus comprises first and second electrodes in electrical contact with the heart, a third indifferent electrode and means for switching connected to the first and second electrodes. The switching means switches the first and second electrodes alternately between a sensing mode and a stimulating mode. In the stimulating mode, the first and second electrodes are maintained at equal electrical potentials, and in the sensing mode, the switching means opens the circuit between the first and second electrodes so as to allow the first and second electrodes to operate as bipolar sensing electrodes. The first and second electrodes are further connected to a means for providing a differential signal having a first input for receiving the signal from the first electrode, a second input for receiving the signal from the second electrode and having an output which provides a sensing signal substantially equivalent to the difference in potentials between the first and second electrodes.

In yet another aspect of the invention, an improved apparatus for applying an electrical potential to body tissue and sensing the response to the applied electrical potential is provided. In this aspect, the apparatus comprises means for generating the electrical potential, a first electrode in electrical contact with the body tissue which provides a first response signal, and a second electrode in electrical contact with the body tissue which provides a second response signal. The apparatus further comprises a third indifferent electrode in electrical contact with the body tissue which is adapted to transmit the electrical potential from the generating means to the body tissue. Means for switching is connected to the first and second electrodes wherein the switching means switches the first and second electrodes alternately between a sensing mode and a transmitting mode. In the transmitting mode, the first and second electrodes are maintained at equal electrical potentials and are arranged to further transmit the electrical potential from the generating means through the body tissue. In the sensing mode, the switching means operates between the first and second electrodes so as to cause the first and second electrodes to act as bipolar sensing electrodes. Means for providing a differential signal including a first input for receiving the first response signal from the first electrode and a second input for receiving the second response signal from the second electrode. The differential signal means outputs the measured response signal.

In yet another aspect of the invention, an improved apparatus for sensing a response in body tissue is provided wherein the response results from an electrical potential applied to the body tissue for a limited duration. The improved apparatus comprises a first electrode in electrical contact with the body tissue which provides a first response signal, a second electrode in electrical contact with the body tissue which provides a second response signal and a third indifferent electrode in electrical contact with the body tissue. Means for switching is connected to the first and second electrodes. The switching means operates in a first switch position to short circuit the first and second electrodes together during application of the electrical potential. In a second switch position, the switching means operates to open the short circuit so as to cause the first and second electrodes to act as bipolar sensing electrodes. Means for providing the differential signal is connected to the first and second electrodes for receiving the first and second response signals.

In yet another embodiment of the invention, apparatus is provided wherein first and second sensing electrodes are shorted to ground during application of external stimulus in order to prevent saturation of the sensing differential amplifier.

BRIEF DESCRIPTION OF THE DRAWINGS

The foregoing and other objects, features and advantages of the invention will be apparent from the following more particular description of the preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Referring now to FIG. 1, the apparatus as provided in one embodiment of the invention is shown schematically. The apparatus comprises a means for generating electrical potential 10, indifferent electrode 12, lead 20 including first electrode 24 and second electrode 30, first and second switches 40 and 42 and differential amplifier 50. The generating means 10 has output lines 5 and 7 for delivering an electrical potential to body tissue. Generating means 10 may be, for example, any well known pulse generation device or cardiac pacemaker device. In the example of the invention shown in FIG. 1, the first and second electrodes may advantageously be a tip electrode and a ring electrode as is typically used in pacemaker apparatus. Electrode 12 may be a bipolar ring or other current path such as the pacer case in the case of a pacemaking application or, for example, a defibrillator shocking lead or patch electrode in the case of an embodiment of the invention in a defibrillator device. Such patch electrodes are well-known in the art. The invention is described further hereinbelow in terms relating to a heart pacemaker, but it will be understood that this description is meant by way of illustration and not limitation of the invention.

Electrode 24 and electrode 30 may, in one advantageous embodiment of the invention, have differing surface areas. Electrode 24 surface area may advantageously be ten times less than the electrode surface area of electrode 30 to increase the differential signal sensed by the differential amplifier 50.

Tip electrode 24 is connected by means of lead 25 to the switching arm 40C of switch 40. Similarly, ring electrode 30 is connected by means of lead 35 to the switching arm 42C of switch 42. Switches 40 and 42 are preferably solid state switches which may advantageously be C-MOS FETs having low ON resistance characteristics or equivalent solid state switching devices. Alternatively, as is shown in FIG. 2, the solid state switching may be accomplished through the use of blocking diodes 60A and 60B. Note that if the polarity of the pulse generator 10 were reversed, those skilled in the art will appreciate that the diodes and/or other solid state switching devices would be configured accordingly to maintain the operational characteristics of the invention.

As is best illustrated in FIG. 1, differential amplifier 50 has first and second differential inputs 52 and 54. The first differential input is connected to terminal 40A of switch 40 and the second differential input is connected to terminal 42A of switch 42. The B terminals of switches 40 and 42 are connected in common to line 7 which is the return stimulation lead from the pulse generator 10. Differential amplifier 50 provides a differential output S which comprises the difference between the signals appearing on the first and second inputs 52 and 54 respectively. Differential amplifier 50 may be any suitable differential amplifier as is conventionally available.

Having described the apparatus and configuration of the invention, the operation of the invention will now be described in order to aid in the understanding of the principles of the invention. Referring again to FIG. 1, in this aspect the invention operates in two modes, namely a common mode stimulation mode and a bipolar sensing mode. In the common mode stimulation mode, the solid state switches 40 and 42 are arranged so as to switch the electrodes 24 and 30 through the B terminals providing a common connection to pulse generator line 7. It is to be understood that in operation the lead 20 would normally be implanted in or on the thoracic region and the indifferent electrode 12 would also be making physiological contact with the body or the heart, for example. When a pulse is generated by pulse generator !0, therefore, current I will flow between the indifferent electrode 12 and the tip electrode 24 and ring electrode 30 which are connected in common. The circuit is, therefore, completed through the electrodes to lead 7. Since electrodes 24 and 30 are connected together, they will have the same electrical potential.

Having stimulated the heart or other target organ or body tissue as described above, the switches 40 and 42 are then operated to route signals from the tip electrode 24 and ring electrode 30 through the A terminals of the switches to the first and second inputs of the differential amplifier 50. Note that in an embodiment of the invention employing diodes (as shown in FIG. 2) or equivalent semiconductor devices, it is not necessary to provide an external control signal to accomplish this switching. The diodes simply route the stimulating current through the pulse generator in the stimulation mode and act as an open switch between leads 25 and 35 when the stimulating pulse is terminated. Therefore, in the configuration shown in FIG. 2, the differential amplifier is always connected to the first and second electrodes, but the circuit operates to effectively short the first and second electrodes together when stimulation current flows through the diodes and opens the circuit between the two electrodes after termination of the stimulation current. Thus, in either the configuration shown in FIG. 1 or FIG. 2, the tip electrode 24 and the second ring electrode 30 operate as bipolar sensing leads essentially instantaneously after termination of the stimulation pulse. Since the tip electrode 24 and the ring electrode 30 are connected together during the stimulation signal, they will experience the same after-potential signal. In accordance with the invention, the leads 24 and 30 are routed to differential inputs of the differential amplifier 50 and the differential amplifier 50 provides the difference in the two signals resulting in elimination of any after-potential signal at output S. Only the evoked response to the stimulation signal will pass through the differential amplifier S as the first tip electrode 24 and second electrode 30 act as bipolar leads. The indifferent electrode 12 is not required in the sensing mode of this apparatus.

In order to further enhance the operation of the apparatus provided by the invention, it is advantageous, although not essential, to match the tip electrode 24 and ring electrode 30 with the same reactive surface area. Note, however, that as long as the electrodes do not vary in reactive surface area by more than a factor of 10, performance will be within acceptable levels. Matching of the electrodes may be accomplished using a porous electrode or an activated porous electrode with an enhanced reactive surface. A useful porous electrode is disclosed in patent application Ser. No. 07/325,764 filed Mar. 20, 1989 entitled "Porous Electrode With Enhanced Reactive Surface", the teachings of which are incorporated herein by reference.

While the description of the invention above is provided in terms of its application to heart pacemaker apparatus, those skilled in the art will recognize that the invention is not so limited. For example, with reference to FIG. 3, the teachings of the invention may be employed to provide an apparatus which senses a physiological response to an electrical potential applied by electrodes other than electrodes 24 and 30. In such a case, the means for generating electrical potential will not be electrically connected to electrodes 24 and 30. In such a case, the first and second electrodes will be held at a local isolated electrical ground, for example, in order to assure that the electrodes 24 and 30 remain at an equal potential during the application of an electrical potential by another external source.

Figure 3:
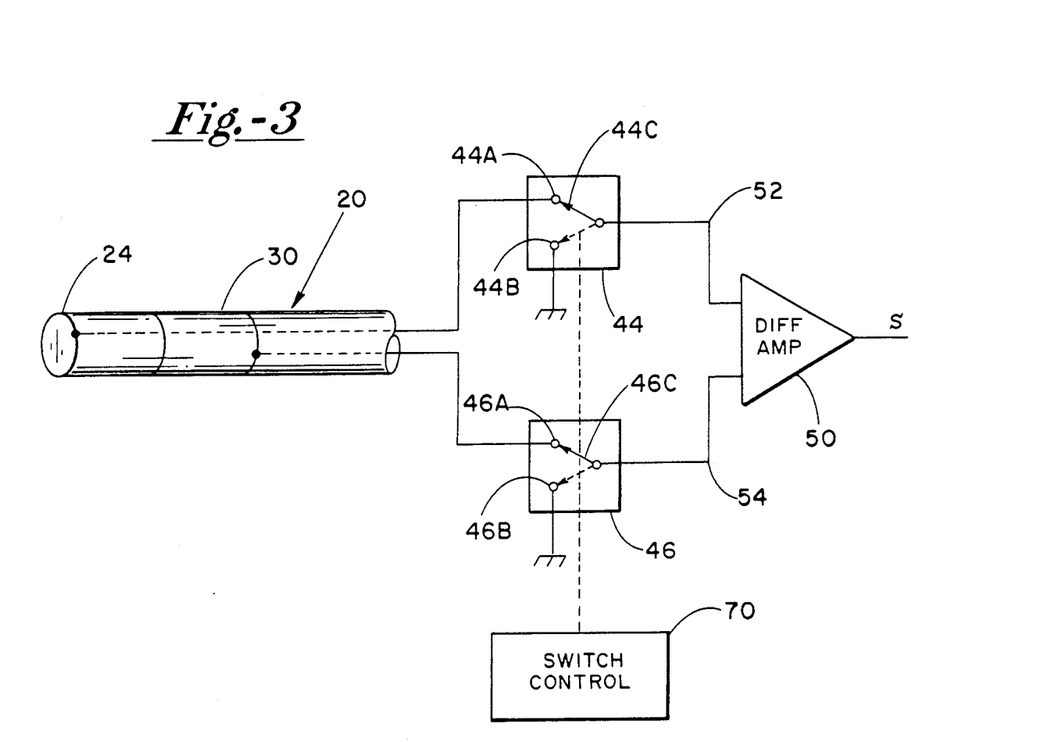
FIG. 3 is a schematic diagram of yet another aspect of the invention wherein sensing electrodes are grounded during the application of external stimulus.

Switching in this example is done by means of switches 44 and 46. Switch arms 44C and 46C are controlled by means of a conventional switch control means 70 which appropriately switches upon removal or application of the external stimulus. It may also be advantageous to locate electrodes 24 and 30 on body tissues or organs other than the heart. In such cases an appropriate geometry for the shape of the electrodes must be selected.

FIG. 2 shows one embodiment of the invention utilizing a porous electrode 220. The porous electrode can be advantageously used in various environments to increase the sensitivity of the apparatus. Porous electrodes are well known in the art. Porous electrodes are used to reduce the electrode after potentials such as discussed in assignee3 s application Ser. No. 07/325,764, filed Mar. 20, 1989, entitled "Porous Electrode With An Enhanced Reactive Surface".

Figure 4:
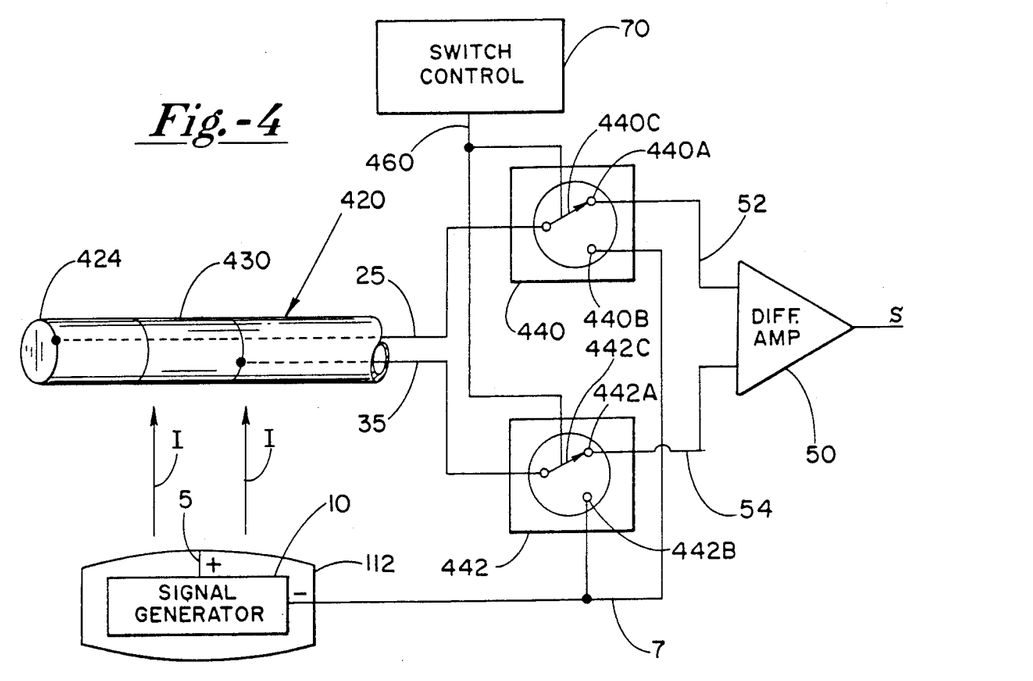
FIG. 4 is a schematic diagram of yet another aspect of the invention employing solid state switching, a porous electrode and a case covering the indifferent electrode.

Referring now to FIG. 4, the apparatus as provided in yet another embodiment of the invention is shown schematically. The apparatus comprises means for generating electrical potential 10, an indifference electrode 112, lead 420 including first electrode 424 and second electrode 430, first and second switches 440 and 442 and differential amplifier 50. The generating means 10 has output line 5 and 7 for delivering an electrical potential to body tissue. The generating means 10 may be, for example, any well known pulse generation device, cardioverter/defibrillator or cardiac pacemaker device. In this embodiment of the invention, indifference electrode 112 is composed of the casing around generating means 10.

In the example of the invention shown in FIG. 4, the first and second electrodes may advantageously be a tip and a ring electrode as is typically used in pacemaker apparatus. Electrode 12 may be a bipolar ring or other current path such as the pacemaker case in the situation of a pacemaking application or, for example, a defibrillator shocking lead or patch electrode in the case of the embodiment of the invention in a defibrillator device. Such patch electrodes are well known in the art. The invention is described further hereinbelow in terms of relating to a heart pacemaker but it should be understood that this description is meant by way of illustration and not a limitation of the invention.

Electrodes 424 and 430 are connected by means of lead 25 to the switching arm 440C of switch 440. Similarly, ring electrode 430 is connected by means of a lead 35 to the switching arm 442C of switch 442. Switches 440 and 442 are preferably solid state switches which may be advantageously CMOS, field effect transistors having low ON resistance characteristics or equivalent solid state switching devices. Alternately as is shown in FIG. 2, the solid state switching may be accomplished by the use of blocking diode 60A and 60B. Note that the plurality of the pulse generator 10 was reversed, those skilled in the art will appreciate that the diodes on other solid state switching devices will be configured accordingly to maintain the operational characteristic of the invention.

Tip electrode 420 may be advantageously constructed out of a porous material thereby increasing the electrical conductivity and electrical contact with surrounding body tissues. The operation of the apparatus in FIG. 4 is substantially equal to the operation of the apparatus of FIG. 1 and the description of the operation of the FIG. 1 device should be referenced for a description of the operation of FIG. 4's device.

FIG. 4 additionally shows a method of switching the solid state switches with mode line 460. When the apparatus of FIG. 4 is in sensing mode the switches are positioned such that the current from line 25 is fed to line 52 to one input of the differential amplifier 50 and current from line 35 is fed to line 54 to the other input of the differential amplifier. Thus, accomplishing the sensing mode operation. In an alternate mode of operation of the apparatus, the switches are permitted to contact the negative lead of the post generator on line 7, thus, completing the stimulus circuit from both line 35 and line 25.

EXPERIMENTAL STUDIES

In experimental studies done at Cardiac Pacemakers, Inc., St. Paul, Minn., three pacing methods were compared, including the method of the invention, bipolar pacing and unipolar pacing. The relative amplitudes of the pacing spike in the evoked cardiac response for each of these methods using bipolar epicardial electrodes was determined.

In the first example, a bipole catheter was used. When bipolar pacing was employed, the pacing spike amplitude for the bipolar pacing was 720 mV. An evoked response could not be detected after the pacing stimulus. During normal sinus rhythm, the QRS amplitude was 19 mV. Thus, the ratio between the pacing spike and the QRS amplitude was 38:1. In contrast, when common mode pacing with bipolar sensing of the invention was employed, the pacing spike amplitude was 50 mV when pacing through both sensing electrodes, reducing the ratio between artifact and QRS amplitude by more than a factor of 10. That is, the pacing stimulus to response ratio was on the order of 2.6:1.

A second experiment using two epicardial electrodes was also done. Using standard unipolar pacing, no evoked response could be seen following the pacing spike artifact. Pacing spikes were typically greater than 500 mV. When the common mode stimulus and bipolar sensing apparatus of the invention was employed, the pacing artifact with both sensing electrodes being employed as cathode was 9 mV. The QRS amplitude during normal sinus rhythm was 6 mV resulting in a pace/normal QRS ratio of 1.5:1. The evoked cardiac response following a pacing stimulus was easily seen, with an amplitude of 3 mV. This resulted in a pace/response ratio of 3:1.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modification, both as to the equipment details and operating procedures, can be accomplished without departing from the scope of the invention itself.

What is claimed is:

1. Apparatus for stimulating and sensing evoked cardiac response to stimulus to a heart with a control signal that indicates a sensing mode or stimulus mode comprising:
   (a) a pulse generator for delivering stimulus signals to the heart;
   (b) a first electrode for electrical contact with the heart which provides a first response signal;
   (c) a second electrode for electrical contact with the heart which provides a second response signal;
   (d) a third indifferent electrode for electrical contact with body tissues that transmits stimulus signals from the pulse generator;
   (e) means for switching connected to the first and second electrodes wherein the switching means switches the first and second electrodes alternately between a sensing mode and a stimulating mode in response to the control signal, wherein in the stimulating mode the first and second electrodes transmit the stimulus signals from the pulse generator through the heart, and in the sensing mode the switching means operates between the first and second electrodes so as to cause the first and second electrodes to act as bipolar sensing electrodes; and
   (f) means for providing a differential signal having a first input for receiving the first response signal from the first electrode and a second input for receiving the second response signal from the second electrode.

2. The apparatus of claim 1 wherein the first and second electrodes each have reactive surface areas wherein the reactive surface area of one electrode is less than 10 times the reactive surface area of the other.

3. The apparatus of claim 2 wherein the first and second electrodes are porous electrodes.

4. The apparatus of claim 2 wherein the first and second electrodes are a type of porous electrodes known as activated porous electrodes.

5. The apparatus of claim 1 wherein the means for switching comprises first and second solid state switches.

6. The apparatus of claim 5 wherein the solid state switches are C-MOS devices.

7. The apparatus of claim 7 wherein the first and second electrodes are a type of porous electrodes known as activated porous electrodes.

8. The apparatus of claim 1 wherein the stimulating signals generated by the pulse generator comprise cardioversion signals.

9. The apparatus of claim 1 wherein the pulse generator includes a case and the third electrode comprises the case of the pulse generator.

10. The apparatus of claim 1 wherein the third electrode comprises a defibrillation electrode.

11. The apparatus of claim 1 wherein the stimulating signals generated by the pulse generator comprise anti-tachycardia stimulation signals.

12. Improved apparatus for sensing a response in body tissue comprising:
(a) a means for generating an electrical potential for electrical contact to the body tissue under the control of a control signal that indicates one of a sensing mode and stimulus mode;
(b) a first electrode for electrical contact with the body tissue which provides a first response signal;
(c) a second electrode for electrical contact with the body tissue which provides a second response signal;
(d) a third indifferent electrode for electrical contact with the body tissue;
(e) means for switching connected to the first and second electrodes wherein the switching means operates in response to the control signal in a first switch position to short circuit the first and second electrodes together during application of the electrical potential and, wherein the switching means operates in a second switch position to open the short circuit so as to cause the first and second electrodes to act as bipolar sensing electrodes; and
(f) means for providing a differential signal having a first input for receiving the first response signal from the first electrode and a second input for receiving the second response signal from the second electrode.

13. The apparatus of claim 12 wherein the means for switching comprises first and second solid state switches.

14. The apparatus of claim 13 wherein the solid state switches are C-MOS devices.

15. The apparatus of claim 12 wherein the first and second electrodes are porous electrodes.

16. The improved apparatus of claim 12 wherein the improved apparatus senses evoked cardiac response and wherein the applied electrical potential comprises cardiac stimulating signals that are heart pacemaker signals and wherein the means for generating electrical potential has a case.

17. The apparatus of claim 16 wherein the stimulating signals comprise anti-tachycardia stimulation signals.

18. The apparatus of claim 16 wherein the heart pacemaker apparatus case is used as the third electrode.

19. The apparatus of claim 12 wherein the third electrode comprises a defibrillation electrode.

20. The apparatus of claim 16 wherein the first and second electrodes each have reactive surface areas wherein the reactive surface area of one electrode is less than 10 times the reactive surface area of the other electrode.

21. Improved apparatus for applying an electrical potential to body tissue under control of a control signal that indicates a sensing mode and transmitting mode and sensing the response to the applied electrical potential comprising:
(a) means for generating the electrical potential;
(b) a first electrode for electrical contact with the body tissue which provides a first response signal;
(c) a second electrode for electrical contact with the body tissue which provides a second response signal;
(d) a third indifferent electrode for electrical contact with the body tissue that transmits the electrical potential from the generating means;
(e) means for switching connected to the first and second electrodes wherein the switching means switches the first and second electrodes alternately between a sensing mode and a transmitting mode in response to the control signal, and wherein in the transmitting mode the first and second electrodes transmit the electrical potential from the generating means through the body tissue and in the sensing mode the switching means operates between the first and second electrodes so as to cause the first and second electrodes to act as bipolar sensing electrodes; and
(f) means for providing a differential signal having a first input for receiving the first response signal from the first electrode and a second input for receiving the second response signal from the second electrode.

22. The apparatus of claim 21 wherein the first and second electrodes are porous electrodes.

23. The apparatus of claim 21 wherein the first and second electrodes are activated porous electrodes.

24. The apparatus of claim 21 wherein the first and second electrodes each have reactive surface areas wherein the reactive surface are of one electrode is less than 10 times the reactive surface area of the other electrode.

25. The apparatus of claim 13 wherein the switching means is connected at one terminal to an electrical ground so as to further operate to electrically ground the first and second electrodes in the first switch position.

26. Improved apparatus for sensing a response in body tissue wherein the response results from an electrical potential applied to the body tissue for a limited duration under control of a control signal, wherein the improved apparatus comprises:
(a) a first electrode for electrical contact with the body tissue which provides a first response signal;
(b) a second electrode for electrical contact with the body tissue which provides a second response signal;
(c) means for switching connected to the first and second electrodes wherein the switching means operates in response to the control signal in a first switch position to ground the first and second electrodes together during application of the electrical potential and, wherein the switching means operates in a second switch position to open the short circuit so as to cause the first and second electrodes to act as bipolar sensing electrodes; and (d) means for providing a differential signal having a first input for receiving the first response signal from the first electrode and a second input for receiving the second response signal from the second electrode.

27. The apparatus of claim 26 wherein the means for switching comprises first and second solid state switches.

28. The apparatus of claim 27 wherein the solid state switches are C-MOS devices.

29. The apparatus of claim 28 wherein the first and second electrodes are porous electrodes.

30. Apparatus for stimulating and sensing evoked cardiac response to stimulus to a heart with a control signal comprising:

(a) a pulse generator for delivering stimulus signals to the heart;

(b) a first electrode for electrical contact with the heart which provides a first response signal;

(c) a second electrode for electrical contact with the heart which provides a second response signal;

(d) a third indifferent electrode for electrical contact with body tissues that transmit the stimulus signals from the pulse generator;

(e) a first diode means connected to the first electrode and having a second terminal, and a second diode means having a first terminal connected to the second electrode and a second terminal connected to the second terminal of the first diode and pulse generator, wherein the diodes allow the stimulation signal to pass through the heart in the first and second electrodes upon receiving a stimulation signal from the pulse generator and to present an open circuit between the first and second electrodes while the apparatus is in the sensing mode of operation; and (f) means for providing a differential signal having a first input for receiving the first response signal from the first electrode and a second input for receiving the second response signal from the signal electrode.

* * * * *

UNITED STATES PATENT AND TRADEMARK OFFICE
CERTIFICATE OF CORRECTION

PATENT NO. : 5,018,523
DATED : May 28, 1991
INVENTOR(S) : Stanley M. Bach, Jr., et. al.

It is certified that error appears in the above-indentified patent and that said Letters Patent is hereby corrected as shown below:

Column 9, line 13 (Claim 7), delete the number "7" and replace it with --6--.
Column 10, line 50 (Claim 25), delete the number "13" and replace it with -- 12 --.
Column 12, lines 23-24, delete the word "signal" and replace it with --second--. (2nd occurrence).

Signed and Sealed this

Eleventh Day of July, 1995

Attest:

BRUCE LEHMAN

Attesting Officer

Commissioner of Patents and Trademarks